United States Patent
Chatterjee (10) Patent No.: US 10,182,945 B2
(45) Date of Patent: Jan. 22, 2019

(54) HYBRID DRESSINGS OF HYDROPHILIC MATERIAL AND POLYMER FOAM

(71) Applicant: Dristi LLC, Cincinnati, OH (US)

(72) Inventor: Ranjit Chatterjee, Cincinnati, OH (US)

(73) Assignee: Dristi, LLC, Cincinnati, OH (US)

(*) Notice: Subject to any disclaimer, the term of this patent is extended or adjusted under 35 U.S.C. 154(b) by 0 days.

(21) Appl. No.: 15/985,700

(22) Filed: May 22, 2018

(65) Prior Publication Data
US 2018/0263823 A1 Sep. 20, 2018

Related U.S. Application Data

(63) Continuation-in-part of application No. 14/463,602, filed on Aug. 19, 2014, now Pat. No. 10,004,646.

(60) Provisional application No. 61/887,256, filed on Oct. 4, 2013.

(51) Int. Cl.
A61F 13/00 (2006.01)

(52) U.S. Cl.
CPC .. *A61F 13/00042* (2013.01); *A61F 13/00012* (2013.01); *A61F 13/00017* (2013.01); *A61F 13/00029* (2013.01); *A61F 13/00068* (2013.01); *A61F 2013/00323* (2013.01); *A61F 2013/00336* (2013.01)

(58) Field of Classification Search
None
See application file for complete search history.

(56) References Cited

U.S. PATENT DOCUMENTS

| | | |
|---|---|---|
| 3,903,232 A | 9/1975 | Wood et al. |
| 4,049,592 A | 9/1977 | Marans et al. |
| 4,110,276 A | 8/1978 | Desmarais |
| 4,613,543 A | 9/1986 | Dabi |
| 4,664,662 A | 5/1987 | Webster |
| 4,752,349 A | 6/1988 | Gebel |
| 4,898,642 A | 2/1990 | Moore et al. |
| 4,969,880 A | 11/1990 | Zamierowski |
| 5,147,345 A | 9/1992 | Young et al. |
| 5,260,345 A | 11/1993 | Desmarais et al. |
| 5,268,224 A | 12/1993 | Desmarais et al. |

(Continued)

OTHER PUBLICATIONS

Borgquist, Ola, et al., "The influence of Low and High Pressure Levels during Negative-Pressure Wound Therapy on Wound Contraction and Fluid Evacuation", Plastic and Reconstructive Surgery Journal of the American Society of Plastic Surgeons, vol. 127, No. 2, pp. 551-559, 2011.

(Continued)

*Primary Examiner* — Kim M Lewis
(74) *Attorney, Agent, or Firm* — United IP Counselors, LLC (57) ABSTRACT

Disclosed are hybrid wound dressings that include at least one front layer of a hydrophilic absorbent material and at least one layer behind the front layer that is made of an open-celled polymeric foam made from high internal phase emulsions (HIPEs). The hydrophilic absorbent material may be a natural polymeric material; a synthetic, non-foam polymer; or a material like glass microfiber. Each layer has a rate of fluid absorption and a capillary suction pressure (CSP) for a working fluid like blood plasma. The CSP increases from the front layer toward the layers behind the front layer, such that fluid is drawn away from a wound.

18 Claims, 6 Drawing Sheets

(56) References Cited

U.S. PATENT DOCUMENTS

| | | | |
|---|---|---|---|
| 5,318,554 | A | 6/1994 | Young et al. |
| 5,331,015 | A | 7/1994 | Desmarais et al. |
| 5,387,207 | A | 2/1995 | Dyer et al. |
| 5,633,291 | A | 5/1997 | Dyer et al. |
| 5,636,643 | A | 6/1997 | Argenta et al. |
| 5,650,222 | A | 7/1997 | Desmarais et al. |
| 5,795,921 | A | 8/1998 | Dyer et al. |
| 6,274,638 | B1 | 8/2001 | Yonemura et al. |
| 6,903,243 | B1 | 6/2005 | Burton |
| 7,521,587 | B2 | 4/2009 | Busam et al. |
| 7,744,576 | B2 | 6/2010 | Busam et al. |
| 8,198,505 | B2 | 6/2012 | Hird et al. |
| 2015/0119837 | A1* | 4/2015 | Thompson, Jr. ........ A61L 15/26 604/369 |
| 2015/0328060 | A1* | 11/2015 | Bagger-Sjoback ... A61F 13/537 604/369 |
| 2015/0353699 | A1 | 12/2015 | Foudazi et al. |
| 2015/0374876 | A1* | 12/2015 | Hubbard, Jr. ........... A61L 15/26 502/402 |
| 2017/0267827 | A1 | 9/2017 | Rowan et al. |

OTHER PUBLICATIONS

Guillaume, Chaby, et al., "Dressings for Acute and Chronic Wounds A Systematic Review", Arch Dermatol, vol. 143, No. 10, pp. 1297-1304, Oct. 2007.

* cited by examiner

HYBRID DRESSINGS OF HYDROPHILIC MATERIAL AND POLYMER FOAM

CROSS-REFERENCE TO RELATED APPLICATIONS

This application is a continuation-in-part of U.S. application Ser. No. 14/463,602, filed Aug. 19, 2014, which claims priority to U.S. Provisional Application No. 61/887,256, filed Oct. 4, 2013. The contents of both of those applications are incorporated by reference in their entireties.

BACKGROUND OF THE INVENTION

1. Field of the Invention

In general, the invention relates to methods of using polymer foam absorbent materials in wound dressings.

2. Description of Related Art

Since time immemorial, the standard dressing for a wound—the material used to cover a wound, protect it, and absorb blood and other exudates—has been cotton or cotton gauze. Cotton, itself a natural cellulose polymer, is cheap, plentiful, absorbent, and relatively easy to sterilize. Cotton gauze, in pads and rolls, is extremely common in first aid, ambulance, and hospital settings.

Despite its ubiquity, cotton gauze has drawbacks. For example, while it is absorbent, it will not draw and sequester fluids and other exudates away from a wound, and it may thus allow bacteria and other harmful elements to remain in contact with the wound and the patient's skin. On a more practical level, once used, cotton gauzes tend to harden and stick to wounds, making them painful to remove and presenting the possibility that removing a used bandage may cause damage or impede healing. However, despite its potential drawbacks, gauze is still a preferred dressing when its advantages outweigh its drawbacks. For example, particularly with acute injuries and bloody wounds, gauze can help to coagulate blood and to stop bleeding.

In recent decades, doctors and scientists have come to understand the healing process better. For example, it is now known that moisture is helpful in revascularization and other stages of the healing process, and that it may be helpful if the edges of a wound are kept dry while the interior of the wound is kept moist. However, even though the understanding of the process has improved, chronic wounds, like decubitus ulcers, pressure sores, venous stasis ulcers, infected wounds, deep and open surgical incisions, and burns still present long-term problems and require special care. These chronic types of wounds can require weeks or months to heal, and can easily become infected or cause other complications if not treated adequately. Moreover, there are widely varying opinions on the proper treatment protocols.

While caring for chronic wounds is difficult, and standards of care are still evolving, there is evidence that treatments like negative pressure wound therapy (NPWT) can speed healing. In NPWT, a special, sealed dressing is connected to a pump. The dressing may be, for example, an open-celled foam with an average cell size of greater than about 400 µm that is present to act, essentially, as a filter for the pump—it is typically rigid enough that it will not collapse into the pump, and its cells and structure allow fluid to flow through it under vacuum. When the pump is activated, sub-atmospheric pressures are maintained on a wound. Most commonly, negative pressures between −10 and −125 millimeters of mercury (mm Hg) are used.

While treatment protocols may vary considerably, it has become clear that wound dressings play an important role in wound healing, and scientists and engineers have risen to the challenge of creating more sophisticated materials to use as dressings. For example, moist dressings made with hydrocolloids and hydrogels are known, as are dressings made with polymer foams.

Materials have also been developed for absorptive applications other than wound dressing. For example, the Procter and Gamble company of Cincinnati, Ohio has created an open cell, collapsed polymer foam material, marketed as INFINICEL® in the United States, that is sold primarily for use in menstrual pads. This material, made by polymerizing a high internal phase emulsion (HIPE), is highly absorbent, lightweight, and flexible. In particular, U.S. Pat. No. 5,795,921 to Dyer et al., which is incorporated by reference herein in its entirety, discloses formulations and methods for making this kind of polymer foam such that it has pore sizes appropriate for capturing blood and menses.

The Dyer patent does mention briefly that these types of materials can be used in wound dressings, but does not offer any specific guidance on how they might be used.

SUMMARY OF THE INVENTION

One aspect of the invention relates to a method for dressing a wound. The method comprises dressing the wound with a wound dressing that includes at least contiguous layers of foam. The first layer serves as a face or wound-facing layer of foam, and the second layer serves as a back layer. The first and second layers of foam may be formed by polymerization using a high internal phase emulsion (HIPE), and may have generally homogenous mean cell sizes and, generally homogenous hole sizes between adjacent cells, that form a gradient from a larger, generally homogenous mean cell size and a larger, generally homogeneous hole size, in the first, face layer to a smaller, generally homogenous mean cell size and a smaller, generally homogenous hole size in the second layer. At least one of the two layers may be a collapsed layer of foam, and in some cases, the second or back layer will be a collapsed layer of foam, while the first or face layer will be a layer of expanded foam. In some embodiments of the invention, the wound dressing may have several layers of foam, arranged in a gradient such that the first or face layer has the largest cell and hole sizes and the second or back layer has the smallest cell and hole sizes, and there are layers of foam with intermediate cell and hole sizes between the first and second layers. The method may also comprise replacing the wound dressing once it becomes partially or fully saturated.

In methods according to this aspect of the invention, the negative capillary pressure exerted by a wound dressing on a wound may reduce or obviate the need for negative pressure wound treatment (NPWT). However, in some cases, the methods according to embodiments of the invention may be used in conjunction with NPWT.

Another aspect of the invention relates to the structure and composition of wound dressings made with HIPE foam. As was described above, these dressings will typically include at least two generally homogeneous layers of HIPE foam, with different mean cell and hole sizes in each layer of HIPE foam forming a gradient from larger to smaller as fluid moves from the outer face of the dressing toward a backing with a controlled rate of moisture transmission layer. Additionally, wound dressings according to embodiments of the invention may have higher levels of moisture and hydratable salts, and may, in some cases, be prepared without additional steps to wash out the hydratable salts and without extensive drying to reduce moisture.

A further aspect of the invention relates to hybrid wound dressings that comprise at least two contiguous layers, including at least one wound-facing layer and at least one backing layer. The at least one wound-facing layer is comprised of a hydrophilic material that is not an HIPE foam, and the at least one backing layer comprises a layer of HIPE foam. The hybrid wound dressing may also include a covering layer overtop the at least one wound-facing layer. The covering layer may have a rate of fluid uptake that substantially matches a rate or rates of fluid uptake of the other layers. Additionally, the capillary suction pressures of the layers may follow a gradient, such that the at least one backing layer has a higher capillary suction pressure than the at least one wound-facing layer.

These and other aspects, features, and advantages of the invention will be set forth in the description that follows.

BRIEF DESCRIPTION OF THE DRAWING FIGURES

The invention will be described with respect to the following drawing figures, in which.

DETAILED DESCRIPTION

The present inventor has found that polymer foam materials made by polymerizing high internal phase emulsions (HIPEs), like the INFINICEL® commercial material marketed by the Procter and Gamble company and the material disclosed in U.S. Pat. No. 5,795,921 to Dyer et al., are particularly suitable for wound care applications. Moreover, the present inventor has also surprisingly found that the capillary pressures exerted by these materials, when they are wetted with fluid, are comparable to at least the lower end of the range of pressures that are commonly used in negative pressure wound treatment (NPWT). Thus, in at least some applications, when an HIPE foam is used in a wound dressing, it may be possible to achieve the effects of NPWT without the difficulty and expense of using a vacuum pump to achieve negative pressure.

Generally speaking, wound dressings according to embodiments of the invention will include at least one layer of an HIPE foam. Optionally, a fluid impervious backing sheet, or a backing sheet with a defined and controlled rate of moisture transmission may be included, as will be described below in more detail. The HIPE foam may be made using the methods disclosed in Dyer et al., cited above, DesMarais et al., U.S. Pat. No. 5,331,015, which is incorporated by reference in its entirety, and other patents that will be set forth below, although some adaptations may be made for wound care applications.

For example, Dyer et al. discloses that hydratable salts, such as calcium chloride, are added to water during the process of forming an HIPE emulsion. The resulting foam is then washed later in the manufacturing process to reduce the level of these salts. In applications in which the object is to create a menstrual pad, this is helpful because menses are typically somewhat viscous, and the presence of salts can increase their viscosity. However, the nature of wound exudates is different; most types of exudates are actually thin and watery. Thus, in wound care applications, it may be possible to omit some of the additional washing steps and allow any ionic salts to remain in the final foam in their existing concentrations.

Additionally, Dyer et al. and other references describe maintaining a low moisture level in the final foam product, typically 2-10%. This facilitates the greatest level of absorption and may be beneficial in other ways, including lower shipping weight and longer shelf life. However, as will be described below in more detail, especially in embodiments where the dressing is intended to reduce or obviate the need for NPWT, a higher initial moisture content may be helpful in achieving and maintaining the material's maximum capillary pressure. Therefore, moisture levels of up to about 20% in the finished HIPE foams may be useful in those embodiments.

While one layer of HIPE foam may be sufficient in a wound dressing for some applications, in many embodiments, it may be particularly advantageous if the wound dressing uses a number of different layers of open cell HIPE foam, each with a different, but generally homogenous, cell size. Commercial HIPE foam products that contain multiple layers of HIPE foam, each layer with different properties, are known in the art, and the Nippon Shokubai Company of Osaka, Japan, among others, has created techniques that can be used to layer HIPE foams and cure them together, reflected, for example, in U.S. Pat. No. 6,274,638 to Yonemura et al., the contents of which are incorporated by reference in their entirety. Of course, the exact method by which multiple layers of HIPE foam are joined into a cohesive whole is not critical, so long as the resulting multilayer construct is continuous and the method of joining does not substantially interfere with capillary action and flow of fluids.

In some embodiments, multiple layers of HIPE foam may be assembled in a gradient, typically with foam layers having larger cell sizes toward the front or face of the dressing and foam layers having smaller cell sizes toward the rear of the dressing. Some of the foam layers may be expanded, while other foam layers may be collapsed. While the inventor does not wish to be bound by any particular theory, the larger cells of the face layer or layers of HIPE foam may trap erythrocytes (i.e., red blood cells) and other larger components of wound exudates, while the smaller cells of the back layers of HIPE foam continue to exert capillary pressure and to draw fluidic and smaller components of the exudate, potentially including bacteria, proteins, and other detrimental elements, away from the wound.

One method of selecting appropriate layers of HIPE foam for a dressing with a multilayer gradient is to measure the capillary suction pressure (CSP) of the HIPE foam using deionized water as the test fluid and to arrange the HIPE foam layers in a dressing such that the CSP increases from the front toward the back of the dressing.

As one example, a wound dressing according to one embodiment of the invention may have a free absorbent capacity of about 10-100 grams of exudate per gram of material (g/g); a face layer of open-celled HIPE foam having cells with an average size of about 20-180 μm and holes between adjacent cells of about 10-30 μm; a back layer of open-celled HIPE foam having cells with an average size of less than about 50 μm, typically about 3-35 μm, and a hole size between adjacent cells of about 2-30 μm; and intervening layers, if present, with foam having cells with an average size in the range of about 40-80 μm, and a hole size between adjacent cells of about 2-30 μm. In this exemplary embodiment, the back layer may be a collapsed foam with a glass transition temperature ($T_g$) of about 35° C. or less. In some embodiments, the HIPE foam of the back layer may have residual hydratable salts in the range of about 1-20% by weight, although, as was described above, the amount or concentration of residual hydratable salts may not be of great concern in all embodiments.

Figure 1:
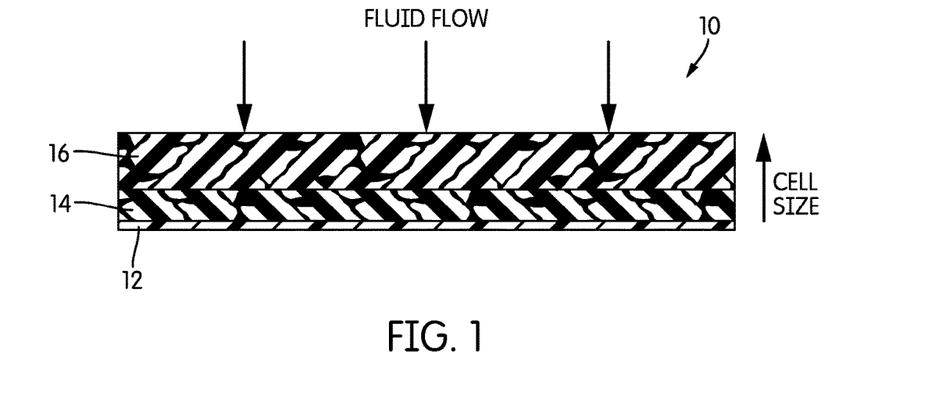
FIG. 1 is a schematic cross-sectional view of a wound dressing according to one embodiment of the invention.

FIG. 1 is a schematic cross-sectional view of an exemplary wound dressing, generally indicated at 10, according to one embodiment of the invention. The wound dressing 10 of the illustrated embodiment includes a film 12 with a controlled rate of vapor transmission, a back layer 14 of an open cell HIPE foam with an average cell size and an average hole size between cells, and a wound-facing front or face layer 16 of an open cell HIPE foam with a different average cell size and a different average hole size. The back layer 14 is a collapsed open cell HIPE foam with an average cell size of 2-20 μm and a thickness of about 0.5 mm collapsed and about 3.0 mm expanded. The second foam layer 16 is an expanded open cell foam with a mean cell size of about 20-50 μm and a thickness of 1-3 mm. If present, the film 12 with its defined moisture transmission rate may extend around the sides of the dressing as well.

However, the film 12 may be an optional component in at least some embodiments. The presence of such a film may prevent bacteria and other wound pathogens from transferring to and infecting caregivers and surfaces around the patient. While that is an advantageous, and sometimes vital, function, a film 12 that is substantially impervious may also prevent the evaporation of aqueous wound exudates, and thus, shorten the life of the wound dressing and potentially affect the rate of healing.

For that reason, the film 12 may have any of a wide range of moisture vapor transmission rates (MVTRs), ranging from 0 grams per square meter per day to about 8,000 grams per square meter per day, with a typical film 12 having an MVTR in the range of 800-3000 grams per square meter per day. While the accepted method for MVTR measurement for impervious backing materials using pure water is convenient and helpful for guidance, a better predictor of dressing performance in duration of use and moisture loss is to test dressing with whole blood or blood plasma in a continuous dosing protocol where real use conditions are simulated. The lack of a film 12, or the presence of a film 12 with a higher MVTR, could allow the back layer 14 of HIPE foam in a wound dressing 10 to re-collapse as fluid evaporates from it, potentially restoring a higher capillary pressure and prolonging the life of the wound dressing 10.

In some embodiments, a cover, typically of a non-woven hydrophilic material, may be provided for the front face of the dressing 10 that faces the wound. However, in wound care applications, particularly when capillary pressure from the dressing 10 is to replace or supplement NPWT, it may be more advantageous to use no cover or intervening layer between the HIPE foams and the wound, such that the maximum amount of fluid can be readily drawn into the HIPE foams. As was described briefly above, higher initial moisture content in the wound dressings 10 may facilitate higher sustained capillary pressures and better performance of the dressings 10.

General guidelines for making suitable HIPE foams for absorbent applications are given in the Dyer et al. patent and in a number of other patents, including U.S. Pat. Nos. 5,331,015; 5,387,207; and 5,650,222, all of which are incorporated by reference in their entireties. While these patents disclose any number of monomers and crosslinkers, preferred monomers are acrylates and styrenes. Calcium chloride and sodium chloride may be preferred salts for hydrophilization. Preferred emulsifiers include diglycerol monoesters. For a high ratio HIPE foam, a second emulsifier may also be used.

With respect to the wound dressing 10 of FIG. 1, the volume to weight ratio of the water phase to the oil phase of the HIPE emulsion is typically in the range of about 17:1 to 50:1 for the front or facial layer 16 and about 23:1 to 125:1 for the back layer 14. Any intervening layers may have ratios of, for example, about 30:1 to 80:1.

Many different materials can be used for the film 12, depending on the use to which the dressing 10 is to be put and the desired rate of fluid evaporation out of the dressing 10. Suitable materials include, but are not limited to, ARGOMEDPLUS® 18411 polyurethane film (3000 MVTR) and TX 1540 polyurethane film (900 MVTR) from Argotec, LLC (Greenfield, Mass.), MICROPORE™ surgical tape (3M, Inc., St. Paul, Minn.) (>3000 MVTR), and polyethylene film of 1 mil thickness (<10 MVTR) (Brentwood Plastics, Inc., St. Louis, Mo.). In some embodiments, the film 12 may be transparent or at least translucent and lightly pigmented, such that it can serve as a visual indicator of when a dressing might require changing. In that case, a light yellow or pink color, indicating that wound exudate had saturated the dressing, might indicate the need for a dressing change.

Wound dressings 10 according to embodiments of the invention may be used in any situation in which a general wound dressing might be used, and they may be made in a variety of shapes and sizes to accommodate wounds of various sizes that are situated in various places on the body. However, they may be particularly helpful with complex, difficult, and chronic wounds, like decubitus ulcers, pressure sores, venous stasis ulcers, infected wounds, deep and open surgical incisions, and burns. They may be used, for example, after surgical wound debridement, to heal skin burns, and to promote skin graft attachment after surgery.

As was described briefly above, wound dressings 10 according to embodiments of the present invention exert maximum capillary pressure when they are wetted and maintain continuous fluid contact with the surface of the wound. For that reason, when a wound dressing 10 is placed on a wound, it may be helpful to secure it in a way that exerts at least sufficient compressive pressure to keep it in contact with the wound. That may involve, for example, securing it with tensioned surgical adhesive tape or wrapping the dressing with roller gauze or self-adhering roller material. Other means of securing dressings are well known to those of skill in the art and may be used in embodiments of the invention. In some embodiments, the dressing 10 itself may include adhesive strips or flaps sufficient to secure the dressing 10.

Of course, in embodiments where a wound dressing 10 is not intended to reduce or obviate the need for NPWT, continuous direct contact with the wound may not be necessary.

Typically, methods for using wound dressings 10 according to embodiments of the invention would involve placing dressings on wounds and replacing those dressings, at intervals, as they became at least partially saturated with wound exudates, or otherwise at regular intervals. For example, the film 12 may be translucent, and the dressing 10 may be replaced when the back layer 14, visible through the backing 12, becomes uniformly discolored. In applications in which the user desires to reduce or obviate the need for NPWT, a dressing 10 may be replaced when the dressing is, for example, up to 50% saturated.

In determining whether a wound dressing 10 can obviate or reduce the need for NPWT, it may be helpful to consider that the standard pressures used in NPWT are predictive of fluid removal via evaporation once the bulk of accumulated wound fluid is removed, whereas the NPWT dressing creates a capillary suction that is effective in removing both accumulated and interstitial fluid as long as there is a fluid continuity between the wound tissue and the dressing at microscopic level. Therefore, wound dressings 10 according to embodiments of the invention may be helpful in a wider range of situations than a direct comparison of NPWT pressure to capillary pressure might indicate.

Although wound dressings 10 according to embodiments of the invention may reduce or obviate the need for NPWT, in some cases, they may be used in conjunction with NPWT, particularly where pressures higher than the capillary pressures exerted by the wound dressings 10 are desired. If wound dressings 10 according to embodiments of the invention are used in conjunction with NPWT, two basic methods may be used. In the first method, NPWT would be administered as usual using a conventional dressing for a period of time, after which the patient would be switched to a wound dressing 10 according to embodiments of the invention. This set of steps might be repeated, so that the patient would receive repeated intervals of conventional NPWT, followed by intervals of coverage with a wound dressing 10.

In a second method of using a wound dressing 10 in conjunction with NPWT, a wound dressing 10 according to an embodiment of the invention would be used as the dressing during NPWT. If the wound dressing 10 is used as an NPWT dressing, it may be perforated to improve air and fluid flow through the dressing. For example, 2-4 perforations per square centimeter, each about 0.5-1.5 mm in diameter, may be formed in the dressing 10.

Generally speaking, whether or not wound dressings 10 according to embodiments of the invention are used alone or as adjuncts to NPWT, they may be used and changed according to schedules or treatment guidelines that assume or expect greater ability to draw fluid away from a wound, prevent maceration around the wound and, in some cases, assume faster healing.

In addition to the methods described above, wound dressings 10 according to embodiments of the invention may be used in methods of monitoring the bacterial load of a wound, or for monitoring for the presence of particular microorganisms. Those methods would typically involve periodically culturing for microorganisms and may alternatively or additionally involve biochemical analysis of inflammatory mediators (e.g., cytokines) in the material of used wound dressings 10 (i.e., by taking a "punch" of the material) at different times or stages of wound treatment.

In most embodiments, the wound dressing 10 of FIG. 1 has absorbent layers comprised entirely, or nearly entirely, of HIPE foams. However, that need not be the case in all embodiments. Instead, in some embodiments, wound dressings may comprise a hybrid of both HIPE foam layers and other hydrophilic, absorbent materials that are not HIPE foams.

Figure 4:
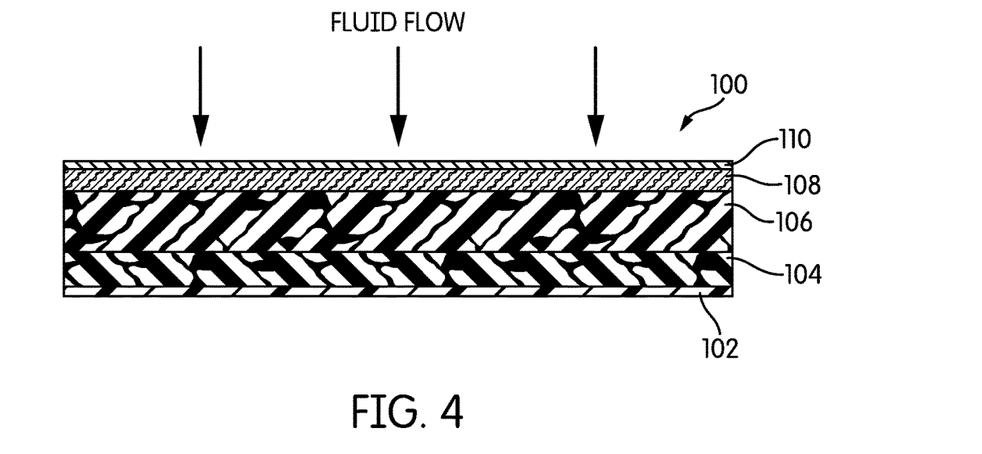
FIG. 4 is a schematic cross-sectional view of a hybrid wound dressing according to another embodiment of the invention.

FIG. 4 is a cross-sectional view of a hybrid dressing, generally indicated at 100, according to another embodiment of the invention. The hybrid dressing 100 comprises both an HIPE foam layer or layers and at least one layer of another hydrophilic, absorbent material. The dressing 100 of the illustrated embodiment includes a backing layer 102, an optional similar to the backing layer 12 of the dressing 10. The dressing 100 also includes two HIPE foam layers 104, 106 that have characteristics similar to the HIPE foam layers 14, 16 of the wound dressing 10, and the description of foam layers 14, 16 applies equally to foam layers 104, 106 unless otherwise noted. For example, the HIPE foam layers 104, 106 may be collapsed layers of foam.

In the illustration of FIG. 4, the dressing 100 also includes a hydrophilic absorbent layer 108 positioned overtop the HIPE foam layers 104, 106. Additionally, a covering layer 110, typically of a nonwoven mesh, faces the wound and serves to reduce adhesion to the wound. Thus, as shown in FIG. 4, fluid flows through the covering layer 110 and the hydrophilic absorbent layer 108 before flowing into and through the HIPE foam layers 104, 106.

The hydrophilic absorbent layer 108 may be made of any hydrophilic material whose properties differ from that of the HIPE foam layers 104, 106. The hydrophilic absorbent layer 108 may be made of a natural polymer, like cellulose, a modified natural polymer, like modified cellulose, or a synthetic polymer, like polyurethane, polypropylene, or polyethylene terephthalate. The hydrophilic absorbent layer 108 may also comprise a material made of glass microfibers. The hydrophilic absorbent layer 108 may be comprised of a polymer foam in some embodiments, but that polymer foam would typically not be an HIPE foam. Examples of materials that may be suitable for use in a hydrophilic absorbent layer 108 are listed in Table 1 below.

TABLE 1

Suitable materials for a hydrophilic absorbent layer.

| Absorbent | Polymer | Capacity (g/g) | Capacity (g/g; Load) | Source/Reference |
|---|---|---|---|---|
| Gauze(GZ) | Cellulose | 12 | 4 | J&J Company |
| Twisted, curled Cellulose(TCF) | Modified Cellulose | 9 | 8 | U.S. Pat. No. 4,898,642 |
| Synthetic foam(PUF) | Polyurethane (100to 400 μm) | 10 | 8 | U.S. Pat. No. 6,903,243 |

TABLE 1-continued

Suitable materials for a hydrophilic absorbent layer.

| Absorbent | Polymer | Capacity (g/g) | Capacity (g/g; Load) | Source/Reference |
|---|---|---|---|---|
| CAPU-CELL ® Synthetic foam | Hypol high density | 10 | 9 | TMP Technologies, Inc., Foam Sciences Division, Buffalo, New York |
| Hydrophilized Nonwoven (HNW) | PP/PET with acrylate coating | 13 | 8 | U.S. Pat. No. 7,521,587 |
| Laminated absorbent polymer(SAPL) | Polyacrylate laminated | 10 | 8 | U.S. Pat. No. 7,744,576 |
| Acrylate microfiber (AMF) | Polyacrylate | 13 | 7 | U.S. Pat. No. 6,903,243 |
| Glass microfiber (GMF) | Polysilicate | 15 | 7 | U.S. Pat. No. 8,198,505 |

The hydrophilic absorbent layer 108 makes the dressing a hybrid dressing, one that has at least some of the advantages of a more traditional hydrophilic absorbent layer and at least some of the advantages of an HIPE-based dressing that were described above.

For example, the addition of the hydrophilic absorbent layer 108 may allow the dressing 100 to retain the high suction pressures offered by HIPE foam layers, but with a layer closer to the wound that will, e.g., promote blood coagulation.

The covering layer 110 is primarily provided to prevent the dressing 100 from sticking to the wound. This may be, e.g., a polyethylene, polypropylene, or high-density polyethylene mesh or apertured film.

The hybrid nature of dressing 100, with its hydrophilic absorbent layer 108, allows the dressing 100 to be used in a variety of contexts and applications. For example, a dressing 100 may be used in acute-care situations where there is considerable bleeding. After 2-3 days, or when the wound begins to heal, a dressing 10 of HIPE foam may be used to manage the wound exudate during healing. When the wound is mostly dry, a dressing 100 may be used again, in order to retain some moisture in the wound as the healing process completes.

In some embodiments, HIPE dressings 10 and hybrid HIPE dressings 100 may be packed and sold together in kit form, so as to offer a complete course of wound dressings for different stages of healing in a single package.

In the description above, cell size and hole size were used as primary descriptors of the properties of the foam layers. However, because the hydrophilic absorbent layer 108 and the covering layer 110 are not foams, for hybrid dressings 100, it may be more convenient to describe layers in terms of their absorbent properties, rather than in terms of their physical structure.

As will be described below in more detail in the examples, each layer 102, 104, 106, 108, 110 can be described in terms of two things: capillary suction pressure (CSP) and rate of fluid intake (R). CSP may be expressed in any convenient units, including millimeters of water, millimeters of mercury, or Pascals, to name a few. Rate of fluid intake is usually in units of mass or volume per unit of time, e.g., grams per minute (g/min). Because CSP and R values may vary depending on the fluid, the relative properties of one layer versus another may be explored by using the same fluid on each, typically a fluid to which the dressing 100 will be exposed in use. This working fluid may be, e.g., water, human blood plasma, or another animal blood plasma, although other working fluids may also be used.

The dressing 100 may implement a CSP gradient similar to the gradient of cell and hole sizes described above with respect to the dressing 10, with the layers toward the back of the dressing (i.e., away from the wound) having the highest CSP values, and the layers toward the front of the dressing, including the hydrophilic absorbent layer 108, having relatively lower CSP values. For example, in the dressing 100, the HIPE foam layer 104 would typically have a higher CSP than the HIPE foam layer 106 that is in front of it.

While the description above emphasizes homogeneous cell size and hole size for HIPE foams, and the foam layers 104, 106 may have the same structure as their counterparts in the dressing 10 described above, the foam layers 104, 106 may also vary somewhat in physical structure so long as they maintain CSP values appropriate for the application.

In most embodiments, it may be helpful if the covering layer 110 has a rate of fluid intake, e.g., a rate of plasma intake, approximately equal to that of the typical rate of intake for HIPE foams, such that the covering layer 110 does not become an impediment to the ingress of fluid into the dressing 100. For example, if the typical rate of blood plasma uptake by HIPE foams is about 1 gram per minute, an appropriate rate of uptake for the covering layer 110 may be at least about 0.9 grams per minute.

For the covering layer 110, another property that may be investigated and used to choose appropriate materials is its potential to adhere to a wound. This may be expressed in comparative, rather than absolute, terms.

In some embodiments, the hydrophilic absorbent layer 108 may also have at least a threshold rate of fluid absorption, so as to not impede fluid flow into the HIPE foam layers 104, 106. For example, the hydrophilic absorbent layer 108 may have a rate of fluid absorption that is at least 90% that of a typical layer of HIPE foam. In practical terms, a rate of plasma absorption of at least about 0.9 g/min, is suitable in at least some embodiments. The rate of fluid absorption of the hydrophilic absorbent layer 108 may be greater than that of a typical layer of HIPE foam, e.g., up to 120% (i.e., 1.2 g/min) that of a typical layer of HIPE foam. In some cases, the rate of fluid absorption of the hydrophilic absorbent layer 108 may be up to 300% that of a typical layer of HIPE foam, i.e., up to 3.0 g/min.

While this description uses the term "wound dressing," which implies an absorbent material placed over the skin to capture blood and other wound exudates, the dressings 10, 100 described here may also be used as wound packing, materials that are inserted into the body cavity, usually during surgical procedures, to apply pressure on internal wounds and to absorb blood during procedures. Thus, the term "wound dressing" should be construed broadly enough to cover wound packing. In cases where the dressings 10, 100 are used as wound packing, a covering layer 100 may be helpful in ensuring that the materials do not stick to internal organs and other structures.

Further details of embodiments of the invention are set forth in the examples below.

EXAMPLES

The following examples serve to illustrate aspects of the present invention.

Example 1: Measurement of CSP in HIPE Foams

HIPE foams with cell sizes ranging from about 10-150 µm were selected for testing for use in composite foam dressings. Table 1 below lists the characteristics of the various foams. In Table 2 below, polymer (I) is made according to the teachings of Dyer et al., U.S. Pat. No. 5,795,921; polymer (II) is made according to the teachings of Dyer et al., U.S. Pat. No. 5,633,291; and polymer (III) is made according to the teachings of DesMarais et al., U.S. Pat. No. 5,331,015. All of those patents are incorporated by reference in their entireties.

TABLE 2

Foam Characteristics.

| Foam Type | Oil/water Ratio | Polymer | Cell Size Range (Av. Hole Size) | Hydratable salt |
|---|---|---|---|---|
| A (expanded) | 1:25 | (I) Acrylate | 30-100 µm (15 µm) | calcium chloride |
| B (expanded) | 1:15 | (II) Styrenic | 20-100 µm (13 µm) | calcium chloride |
| C (collapsed) | 1:60 | (III) Styrenic | 4-20 µm (<5 µm) | calcium chloride |
| D (collapsed) | 1:30 | (I) Acrylate | 2-15 µm (<5 µm) | calcium chloride |

The ability of the individual foam sheets to draw fluid via capillary suction (i.e., their capillary suction pressure (CSP)) was measured using an ascending chromatographic technique. A long strip, typically 2.54 cm×60 cm, was allowed to suspend vertically in a tall glass chamber with ample fluid at the bottom and 1 cm of the lower end of the strip dipped in the fluid. The chamber was kept closed to attain stable humidity. For all capillary suction measurements using water, the temperature of water was maintained at 25° C. For measurements with blood plasma as model of wound fluid, the liquid temperature was 37° C. The extent of the strip above the liquid was maintained at ambient temperature, 24-26° C.

Following a 48-hour period of vertical wicking, the strips were removed and cut into 2 cm pieces for weighing. The maximum wicking height with minimal presence of fluid was used for calculation of capillary suction height in mm, and that maximum capillary suction height equates to CSP as measured in millimeters of water. Table 3 below lists measured capillary suction pressures in mm of water. For purposes of comparison, negative pressures in mm of Hg (mercury) were calculated from the measured units. The densities used for conversion from millimeters of water to millimeters of Hg were 1.05 g/ml and 13.53 g/ml for blood plasma and mercury, respectively.

TABLE 3

Measured CSP of Foams.

| Foam | Wicking Fluid | Capillary Suction Pressure (CSP) in mm Water | Calculated Negative Pressure in mm of Hg | Rate of Plasma Absorption (R; g/min) |
|---|---|---|---|---|
| A | Water | 180 | 13.3 | 0.92 |
|   | Blood Plasma | 200 | 15.5 |  |
| B | Water | 280 | 20.7 | 0.42 |
| C | Water | 430 | 31.8 | 0.08 |
| D | Water | 510 | 37.7 | 0.65 |
|   | Blood Plasma | 470 | 31.0 |  |

As shown in Table 3, all open cell foams showed capillary suction capability in the range of 10 to 38 mm Hg, within the range shown to be useful for NPWT. Of the tested foams, the highest negative pressure was achieved with the foam having the smallest cell size, Foam D, with a mean cell size of 8 µm diameter.

These results also demonstrate that the CSP of Foam D with the smallest cell size has a marginally lower CSP for blood plasma or wound fluid due to the lower surface tension of these biological fluids. The other larger cell foams also show differences in CSP for water versus blood plasma, but within experimental error (which is assumed to be about 10%). However, these examples demonstrate that capillary suction pressure measured with water is predictive of foam performance in exerting negative pressure on a wound.

Example 2: Construction of HIPE Foam Composite Dressings

HIPE foam composite dressings with capillary gradients were created by layering the HIPE foams of Example 1. In constructing these composite gradient dressings, the face layer of the dressing (front layer 16, with respect to the illustration of FIG. 1) had the lowest CSP and foams of increasing CSP were chosen for subsequent layers to create the gradient.

All dressings were evaluated in the laboratory for their ability to absorb blood plasma and store it away from the face layer. Dressing pieces measuring 2.54 cm×2.54 cm were exposed to 1.5 to 2.5 mL warm (37° C.) plasma using a peristaltic pump at the rate of 0.5 mL/hr. The wet dressing was allowed to equilibrate in ambient conditions within sealed environment (thus preventing moisture loss) for 24 hours. After 24 hours, each layer was removed to measure fluid content gravimetrically. The fluid content of the face layer was calculated as percentage of total fluid retained in this layer. Results are presented in Table 3. In Table 4 below, delta CSP values were calculated by adding the differences in CSP values of the face layer and any subsequent layers present in the dressing.

TABLE 4

Multilayer Composite Foam Performance

| Dressing | Backing Layer | First Layer Foam | Intermediate Layer(s) Foam | Second Layer Foam | Calculated Delta CSP (cm) | Face Layer Fluid (%) |
|---|---|---|---|---|---|---|
| Two-Layer Dressings | | | | | | |
| 1 | None | A | None | A | 0 | 49 |
| 2 | None | C | None | D | 8 | 44 |
| 3 | None | A | None | B | 10 | 21 |

TABLE 4-continued

Multilayer Composite Foam Performance

| Dressing | Backing Layer | First Layer Foam | Intermediate Layer(s) | Second Layer Foam | Calculated Delta CSP (cm) | Face Layer Fluid (%) |
|---|---|---|---|---|---|---|
| 4 | None | B | None | D | 13 | 30 |
| 5 | None | B | None | C | 15 | 33 |
| 6 | None | A | None | C | 25 | 13 |
| 7 | None | A | None | D | 33 | 8 |
| Three/Four-Layer Dressings | | | | | | |
| 8 | None | A | B | C | 35 | 8.4 |
| 9 | None | A | C | D | 58 | 6.1 |
| 10 | None | A | B | D | 43 | 4.6 |
| 11 | None | A | B & C | D | 68 | 3.9 |

Figure 2:
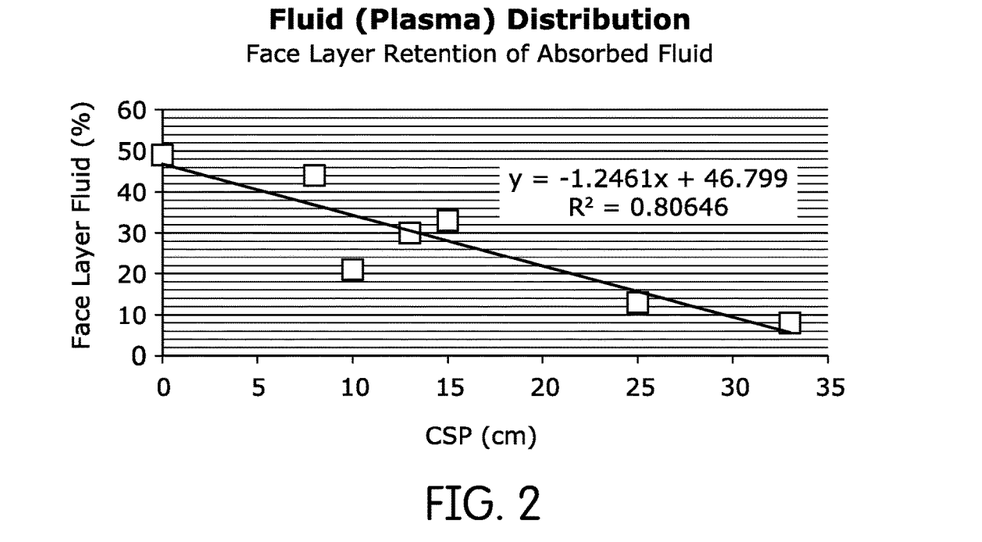
FIG. 2 is a plot of face layer fluid retention of absorbed fluid for different capillary suction pressures, drawn from the data of Example 2.

In Table 4, a lower value of fluid content in the face layer indicated a better performing dressing, in that the dressing created a superior healing environment by drawing moisture away from the skin and leaving minimal wetness of peripheral healthy skin. In FIG. 2, these values are plotted as a function of difference in capillary suction pressures (Delta CSP; water) between the face layer and back layer for two layered composites. Of the tested two-layer composites, the combination of Foam A as the first layer and Foam D as the second layer delivers the highest gradient in suction pressure and minimal (8%) wound fluid next to skin. Of the tested three- and four-layer composites, dressing #11, which used four foams, delivered the highest gradient in suction pressure and the least fluid next to the skin.

Figure 3:
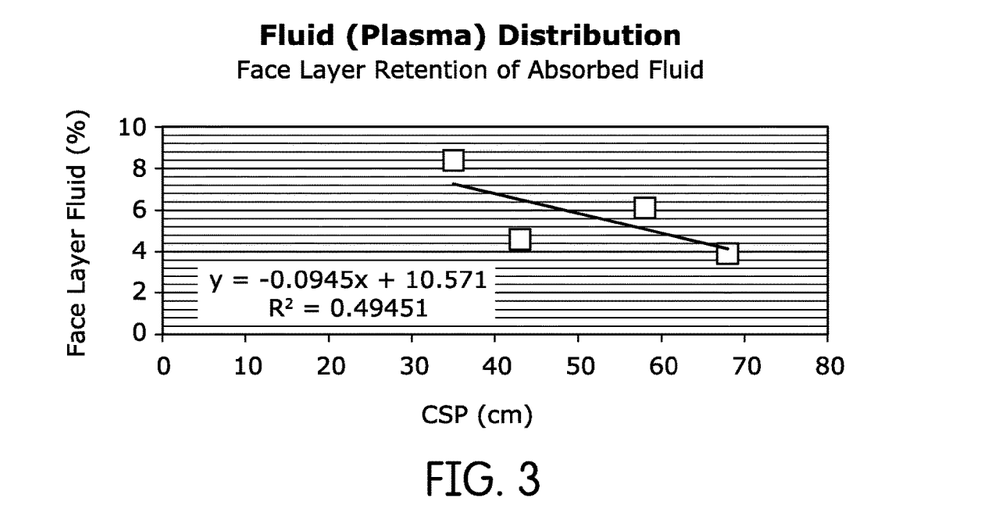
FIG. 3 is another plot of face layer retention of absorbed fluid for different capillary suction pressures, drawn from the data of Example 2.

The relationship between CSP and face layer fluid retention is shown graphically in the plots of FIGS. 2 and 3. Each of those plots illustrates the data from Example 2 and illustrates a regression line for each set of data.

Example 3: Two-Layer Composite Dressing with Backing Film

It is expected that dressings according to embodiments of the invention will be used for long periods of time without the need to change dressings in order to avoid leaks. The long-term performance of dressings was measured using a continuous infusion protocol in the laboratory. A 6 cm×6 cm absorbent dressing was placed face-down on a glass plate and taped around the sides to avoid any moisture loss from areas other than the back/backing film. The face layer was dosed continuously with warm (37° C.) blood plasma at a rate of 0.5 mL/hour until free fluid was observed at the edges of the dressing. The dressing was removed and weighed to calculate moisture loss using the amount of fluid applied and retained at the end of dosing period. The results are shown below in Table 5.

TABLE 5

Duration of use for dressings
Two-layer composite: First layer foam A/Second layer foam D

| Backing | Moisture Loss (%) in 24 hours | Days to Leak |
|---|---|---|
| None | 89 | >10 |
| MICROPORE ™ (Micro apertures) | 79 | 7 |
| ARGOMEDPLUS ®18411 (MVTR ~3000; E96B, Procedure 1.0 mil, 38° C., 90% RH) | 30 | 2 |
| TX 1540 polyurethane film (MVTR ~900; E-96, Procedure B-upright, 23° C. at 50% RH) | 79 | 7 |
| Polyethylene film (1 mil thickness) | <5 | 1.5 |

Example 4: Capillary Suction Pressure of Hydrophillic Materials

Figure 5:
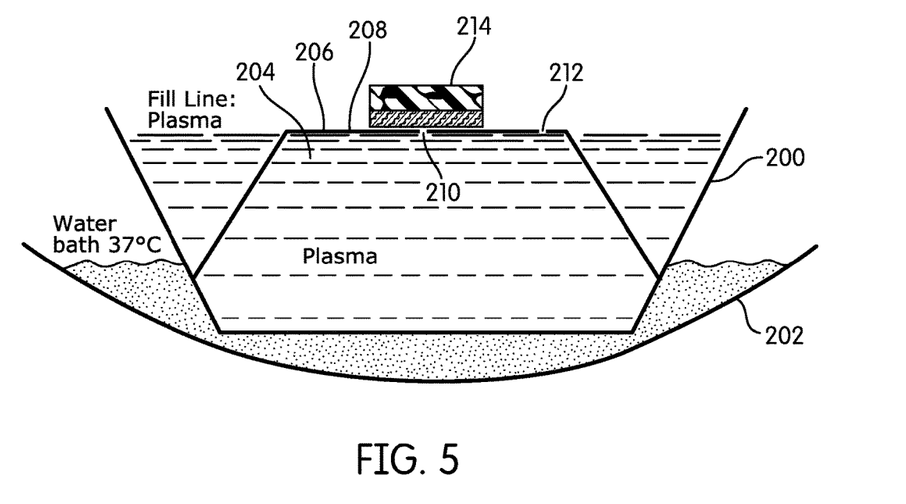
FIG. 5 is a schematic illustration of an apparatus used to determine kinetics of plasma absorption in the dressings of FIGS. 1 and 4.

The ability of absorbent materials to absorb plasma was measured in an apparatus shown schematically in FIG. 5. A container of plasma 200 rests in a hot water bath 202 maintained at 37° C. The plasma 204 is sealed within the container 200 by a lid 206. The lid 206 has a generally flat plateau 208 on center and is perforated twice: a first pinhole 210 approximately in the center of the plateau 208, and a second pinhole 212 for venting off to one side. An absorbent material 214 is exposed to plasma by placing over the first pinhole 210.

Figure 6:
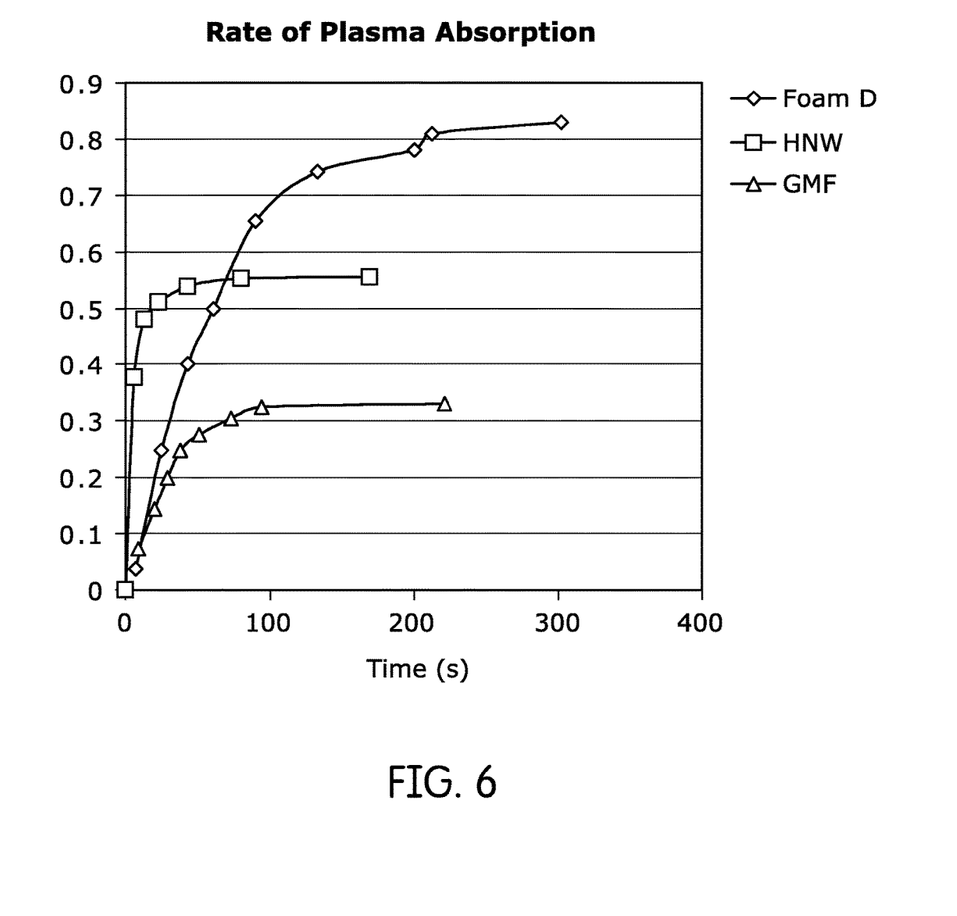
FIG. 6 is a plot of the rate of plasma absorption for foam and non-foam hydrophilic materials for use in a hybrid wound dressing.

A disc of the absorbent material 15 mm in diameter was weighed and exposed to plasma using the apparatus of FIG. 5. Exposure was timed with a stopwatch, and the disc of absorbent material was removed at a regular interval of time and weighed to measure the amount of plasma absorbed. A typical plot for a few of the absorbent materials is shown in FIG. 6. The rate of plasma absorption was calculated using first few points on the steep part of the curve and is expressed as g/min. All plasma absorption rates were measured at 37° C.

Plasma absorption data for the absorbent-layer hydrophilic materials of Table 1 is listed below in Table 6.

TABLE 6

Absorbent Properties of Hydrophilic Absorbent Materials

| Absorbent | Rate of Plasma Absorption (R) g/min | Capillary Suction Pressure (CSP) in mm water | Calculated Negative Pressure in mmHg |
|---|---|---|---|
| GZ | 1.89 | 120 | 8.9 |
| TCF | 2.8 | 68 | 5.0 |
| PUF | 0.04 | 35 | 2.6 |
| HNW | 1.33 | 40 | 3.0 |
| CAPU | 0.09 | 42 | 3.1 |
| AMF | 1.06 | 55 | 4.1 |
| GMF | 0.19 | 33 | 2.4 |
| SAPL | 0.05 | 140 | 10.4 |

As shown in Table 6, with the exception of SAPL and gauze, most of the hydrophilic absorbent materials have modest CSPs and relatively high R-values, as compared with the HIPE foams of Example 1. The materials of Table 6 with high R-values may be uniquely suited for use as a first layer 108 in a composite dressing 100. With modest CSPs, these materials may actually remove fluid from the wound area, as compared with passive flooding of the absorbent.

TCF and HNW stand out for their R-values and wet resilience, a measure of squeeze-out of absorbed fluid upon accidental pressure on the dressing. Gauze may also be a very desirable material when a clinician desires to keep the wound moist. Due to high CSP, it is hard to dry out gauze even with a higher-suction second layer. Additionally, as was noted above, gauze may help an actively bleeding wound to coagulate.

Example 5: Plasma Absorption Rate and Adhesion of Cover Mesh

Measurements of rate of plasma absorption were also taken on a number of prospective cover materials (layer 110; FIG. 4). These were typically PE, PP or HDPE mesh or apertured films, and were obtained from Winfield Laboratories, Inc., Veratec, Inc., and SWM International, and were not characterized beyond the rate studies. A product was made for each cover material using a two-layered HIPE dressing with Foam D as a back layer and Foam A as first or face layer. The rate was measured by exposing the whole product with cover face down on the pinhole 210 of the apparatus of FIG. 5.

The same absorbent HIPE foam core was used for each test of cover material. A qualification criterion for use as a cover material was a plasma absorption rate of at least 0.8 g/min, preferably at least 0.9 g/min. At the end of rate measurement, the pad containing plasma was left to dry on a clean glass plate with the cover face contacting the glass. After 24 hours, the product was lifted off the plate and the effort needed to lift the dried product was scored on a 3-point scale to yield an adhesion score (AS). If the product could be removed from the plate with minimal effort and with no loss of integrity (i.e., no separation of layers), it was assigned an AS of 1. Product removal that required some effort with partial fragmentation of the product was assigned an AS of 2. A score of 3 was assigned to a cover material when wetting or a sharp blade was needed to detach the product.

Figure 7:
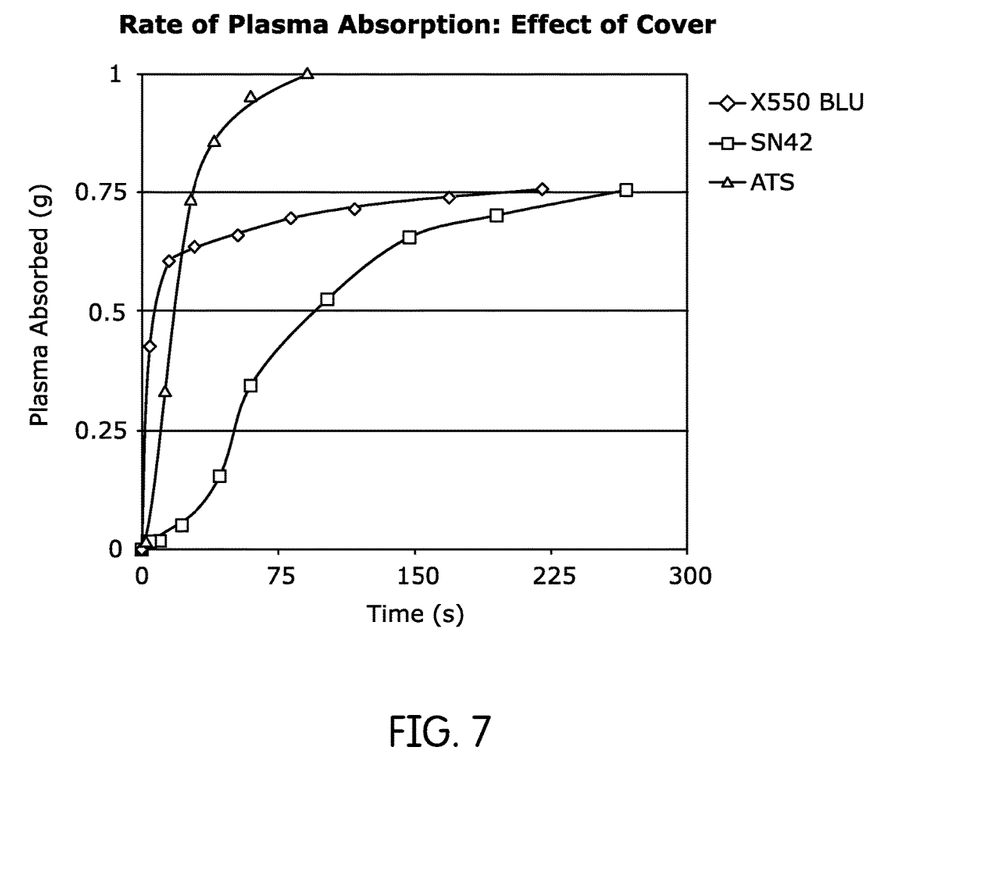
FIG. 7 is a plot of the rate of plasma absorption for a number of materials that might be used as a top covering layer in a hybrid wound dressing.

The adhesion score may be a secondary criterion in selecting cover materials, but it is still worthy of consideration. A high adhesion score indicates that the product is more likely to stick to wounds, which is generally undesirable. The results are in Table 7 below. Additionally, FIG. 7 is a graph of the rate of plasma absorption for three of the materials. As with Example 4 above, the rate of plasma absorption was taken from the steep portions of the curve.

TABLE 7

Plasma Absorption Rate of Cover Mesh

| Cover (Trade name) | Plasma Absorption Rate (g/min) | Adhesion Score (AS) |
|---|---|---|
| N-TERFACE ® | 1.44 | 2 |
| PE/PP Nonwoven | 2.86 | 1 |
| Apertured Nonwoven | 1.81 | 1 |
| H256 | 2.28 | 2 |
| AC530WHTE | 1.8 | 2 |
| K5206PPC | 0.024 | 1 |
| SN42 | 0.3 | 3 |
| X550BLU | 1.35 | 1 |

Example 6: Construction of HIPE Foam Composite Dressings

HIPE foam composite dressings with capillary gradients were created by layering HIPE foams from Example 1 and hydrophilic absorbent materials from Example 4. In constructing these composite gradient dressings, the face layer of the dressing (layer 108, with respect to the illustration of FIG. 4) was a non-HIPE hydrophilic absorbent material, and was matched with a higher CSP HIPE foam layer.

TABLE 7

Multilayer Dressing Construction
(CSP in mm of water, R in g/min)

| First Layer (FL) | Mid Layer (ML) | Second Layer (SL) |
|---|---|---|
| Non-HIPE: R > 0.9, CSP > 30 | None | HIPE: CSP SL > CSP FL |
| Non-HIPE: R > 0.9, CSP > 30 | Non-HIPE or HIPE; CSP ML > CSP FL | Group II; CSP SL > CSP ML |

Table 7 above provides general guidance on the selection of HIPE and non-HIPE materials from Examples 1 and 4 above. In general, HIPE foam in the second (i.e., mid) layer is beneficial for moving fluid away from wound and also allowing the moisture to evaporate off to reduce load in the product and hence allow prolonged use.

All dressings were evaluated in the laboratory for their ability to absorb blood plasma and store it away from the face layer. Dressing pieces measuring 2.54 cm×2.54 cm were exposed to 1.5 to 2.5 mL warm (37° C.) plasma using a peristaltic pump at the rate of 0.5 mL/hr. The wet dressing was allowed to equilibrate in ambient conditions within a sealed environment (thus preventing moisture loss) for 24 hours. After 24 hours, each layer was removed to measure fluid content gravimetrically. The fluid content of the face layer was calculated as a percentage of total fluid retained in this layer. Results are presented in Table 8 below.

TABLE 8

Multilayer Composite Foam/Hydrophilic Absorbent Dressings

| Dressing | First Layer | Intermediate Layer | Second Layer (HIPE Foam) | Face Layer Fluid (%) |
|---|---|---|---|---|
| 1 | HNW | A | D | 0.4 |
| 2 | GZ | A | D | 9.6 |
| 3 | GZ | A | B | 19 |
| 4 | HNW | none | A | 0.4 |
| 5 | TCF | A | A | 4.3 |
| 6 | PU | none | D | 16 |
| 7 | PU | A | D | 14 |
| 8 | HNW | SAPL | D | 1.5 |

In Table 8, a lower value of fluid content in the face layer indicated a better performing dressing, in that the dressing created a superior healing environment by drawing moisture away from the skin and leaving minimal wetness of peripheral healthy skin. Of the tested two-layer and three-layer composites, HNW consistently delivers the lowest levels of wound fluid next to the skin. For gauze products, SAPL is a better intermediate layer than a pure HIPE foam construct. Wounds with high flow rate will be better served with a non-polyurethane composite due to the low rate of plasma absorption.

The composite of HIPE and hydrophilic absorbents will offer about 13 to 35 mmHg negative pressure and relatively higher rate of exudate absorption. These kinds of hybrid dressings may be helpful in managing less complex wounds, or where modest suction is sufficient to stimulate healing. Clinicians will have the choice of managing wound healing environment by choosing a composite dressing, a dressing made entirely of HIPE foam, or by using a combination of composite and HIPE foam dressings at different stages of wound healing, as was described above.

All patent references cited in the text are incorporated by reference in their entireties. Additionally, the term "about," as used herein, refers to a deviation of ±5% relative to the stated value.

While the invention has been described with respect to certain embodiments, the embodiments are intended to be exemplary, rather than limiting. Modifications and changes may be made within the scope of the invention.

What is claimed is:

1. A wound dressing, comprising:
   a first layer of an absorbent hydrophilic material having a first rate of fluid absorption for a working fluid and exerting a first capillary suction pressure (CSP) in absorbing the working fluid; and
   a second layer of open-celled foam produced by polymerizing a high internal phase emulsion (HIPE), the second layer of open-celled foam being generally homogeneous in internal structure, having a second rate of fluid absorption for the working fluid, and exerting a second CSP in absorbing the working fluid, the second layer of open-celled foam being adjacent to and in fluid communication with the first layer of the absorbent hydrophilic material;
   wherein the second CSP is greater than the first CSP.

2. The wound dressing of claim 1, wherein the absorbent hydrophilic material of the first layer comprises one or more constituents selected from the group consisting of cellulose fibers, polymeric fibers, glass fibers, and non-HIPE polymeric foams.

3. The wound dressing of claim 2, wherein the absorbent hydrophilic material of the first layer comprises gauze.

4. The wound dressing of claim 2, wherein the absorbent hydrophilic material of the first layer comprises hydrophilized nonwoven (HNW) material.

5. The wound dressing of claim 2, wherein the first rate of fluid absorption is at least about 0.9 g/min and the working fluid comprises blood plasma.

6. The wound dressing of claim 5, wherein the first CSP is greater than 30 mm water.

7. The wound dressing of claim 6, wherein the second CSP is greater than 100 mm water.

8. The wound dressing of claim 1, further comprising a covering layer of a nonwoven mesh overtop the first layer, the covering layer having a third rate of fluid absorption for the working fluid that is equal to or greater than the first rate of fluid absorption.

9. The wound dressing of claim 1, further comprising one or more intermediate layers of open-celled foam between the first layer of the absorbent hydrophilic material and the second layer of open-celled foam, each of the one or more intermediate layers having a CSP greater than a layer above it and less than a layer below it, such that the wound dressing as a whole has a low-to-high gradient from the first layer toward the second layer.

10. The wound dressing of claim 9, wherein at least one of the one or more intermediate layers comprises an HIPE foam.

11. The wound dressing of claim 10, further comprising a substantially moisture-permeable backing layer behind the second layer.

12. A wound dressing, comprising:
    a cover mesh having a first rate of fluid absorption for a working fluid; and
    a first layer of an absorbent hydrophilic material having a second rate of fluid absorption for the working fluid and exerting a first capillary suction pressure (CSP) in absorbing the working fluid;
    one or more intermediate layers of open-celled synthetic polymer foam, a first of the one or more intermediate layers of open-celled synthetic polymer foam being adjacent to and in fluid communication with the first layer of an absorbent hydrophilic material and ones of the one or more intermediate layers of open-celled synthetic polymer foam behind the first intermediate layer of open-celled synthetic polymer foam being adjacent to and in fluid communication with each other, each of the one or more intermediate layers of open-celled synthetic polymer foam having an individual CSP, each of the individual CSPs being greater than the first CSP and greater than the individual CSP of a prior intermediate layer of open-celled synthetic polymer foam; and
    a rear layer of open-celled foam produced by polymerizing a high internal phase emulsion (HIPE) adjacent to and in fluid communication with a rearmost of the one or more intermediate layers of open-celled synthetic polymer foam, the rear layer of open-celled foam being generally homogeneous in internal structure, having a third rate of fluid absorption for the working fluid, and exerting a third CSP in absorbing the working fluid, the third CSP being greater than the individual CSP of the rearmost of the one or more intermediate layers of open-celled synthetic polymer foam.

13. The wound dressing of claim 12, wherein at least one of the one or more intermediate layers of open-celled synthetic polymer foam comprises an HIPE foam.

14. The wound dressing of claim 12, wherein the absorbent hydrophilic material of the first layer of an absorbent hydrophilic material comprises one or more constituents selected from the group consisting of cellulose fibers, polymeric fibers, glass fibers, and non-HIPE polymeric foams.

15. The wound dressing of claim 14, wherein the absorbent hydrophilic material of the first layer of an absorbent hydrophilic material comprises gauze.

16. The wound dressing of claim 14, wherein the absorbent hydrophilic material of the first layer of an absorbent hydrophilic material comprises hydrophilized nonwoven (HNW) material.

17. The wound dressing of claim 14, wherein the first rate of fluid absorption is at least about 0.9 g/min and the working fluid comprises blood plasma.

18. The wound dressing of claim 17, wherein the first CSP is greater than 30 mm water.

* * * * *